(12) United States Patent
Mitra et al.

(10) Patent No.: US 8,114,448 B2
(45) Date of Patent: Feb. 14, 2012

(54) HERBAL DENTAL CARE COMPOSITION, METHOD OF MANUFACTURING THE SAME AND USE THEREOF

(75) Inventors: Shankar Kumar Mitra, Bangalore (IN); Ramesh Suriyanarayanan, Bangalore (IN); Uddagiri Venkanna Babu, Bangalore (IN); Ekta Saxena, Bangalore (IN)

(73) Assignee: Himalaya Global Holdings Limited, Dubai (AE)

( * ) Notice: Subject to any disclaimer, the term of this patent is extended or adjusted under 35 U.S.C. 154(b) by 856 days.

(21) Appl. No.: 12/139,262

(22) Filed: Jun. 13, 2008

(65) Prior Publication Data

US 2009/0185987 A1      Jul. 23, 2009

(30) Foreign Application Priority Data

Jan. 21, 2008  (IN) .............................. 167/DEL/2008

(51) Int. Cl.
*A61K 36/58* (2006.01)
*A61K 36/00* (2006.01)

(52) U.S. Cl. ........ 424/761; 424/769; 424/777; 424/775; 424/725

(58) Field of Classification Search ........................ None
See application file for complete search history.

(56) References Cited

U.S. PATENT DOCUMENTS

| | | | |
|---|---|---|---|
| 5,496,541 A * | 3/1996 | Cutler | 424/49 |
| 6,562,090 B1 * | 5/2003 | Melbouci et al. | 51/308 |
| 6,730,332 B2 * | 5/2004 | Agarwal et al. | 424/769 |
| 7,074,390 B2 | 7/2006 | MacKinnon | |
| 7,083,779 B2 * | 8/2006 | Behl et al. | 424/58 |
| 2007/0154409 A1 | 7/2007 | Annis | |

FOREIGN PATENT DOCUMENTS

| | | | |
|---|---|---|---|
| JP | 61205207 A * | 9/1986 | |
| WO | WO 2006105615 A1 * | 10/2006 | |

OTHER PUBLICATIONS

JP 61205207 A—abstract translation.*
Asmawi et al. 1993 J Pharm Pharmacol 45:581-584.

* cited by examiner

Primary Examiner — Christopher R. Tate
(74) Attorney, Agent, or Firm — Knobbe Martens Olson & Bear LLP

(57) ABSTRACT

Disclosed herein is a herbal dental care composition comprising extracts of herbs *Punica granatum, Acacia Arabica, Terminalia chebula, Terminalia bellerica, Emblica officinalis* and *Embelia ribes*, optionally extract of *Azadirachta indica* and pharmaceutical acceptable excipients. Also disclosed are the methods of making the composition, formulating the same into different delivery systems and use thereof for preventing various dental diseases.

36 Claims, 1 Drawing Sheet

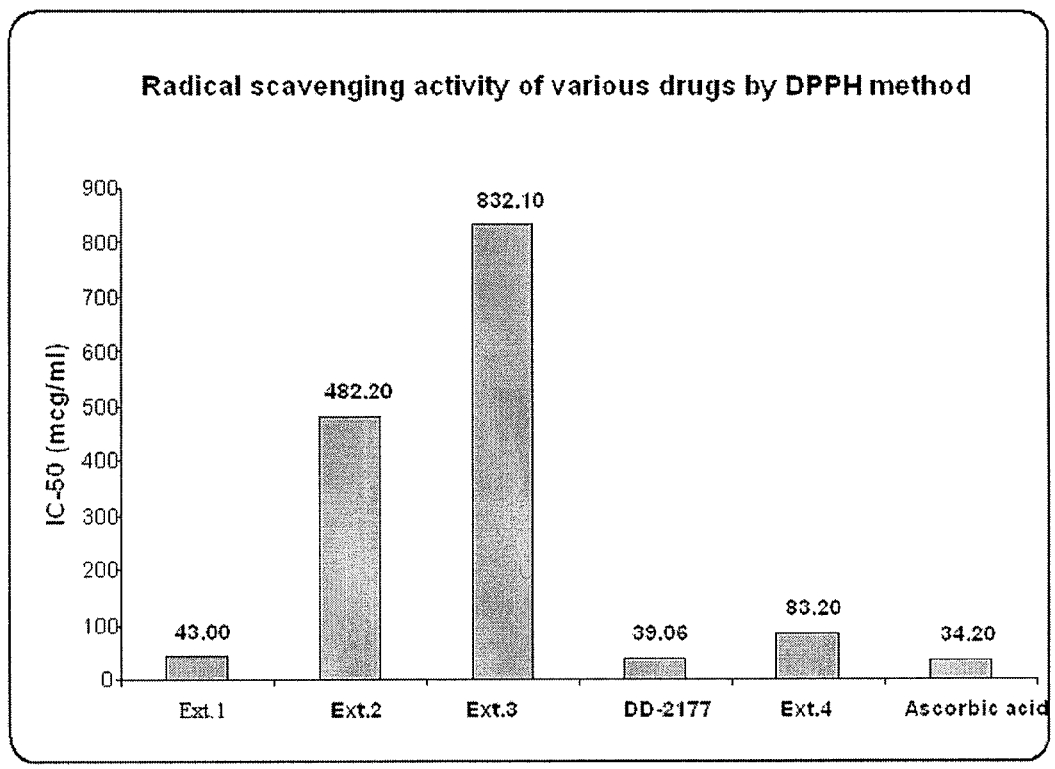
Extract 1: Punica granatum
Extract 2: Acacia arabica
Extract 3: Azadirachta indica
Extract 4: Triphala (T.Chebula, T. Bellerica, E. officinalis)
DD-2177: Herbal blend extract

HERBAL DENTAL CARE COMPOSITION, METHOD OF MANUFACTURING THE SAME AND USE THEREOF

FIELD OF THE INVENTION

This invention, in general relates to a dental care composition. In particular, the present invention provides an herbal dental care composition comprising extracts of *Punica granatum, Acacia arabica, Terminalia chebula, Terminalia bellerica, Emblica officinalis* and *Embelia ribes* and excipients of natural origin, methods of manufacturing the composition and use thereof.

BACKGROUND OF THE INVENTION

Dental care is one of the primary health concerns of people worldwide. The main diseases of teeth include plaque, dental carries and pyorrhoea. The use of various herbal powders for dental diseases is well known in the prior art.

There are many dentifrices in the form of paste, gel and powders available for cleaning, whitening and preserving teeth. These compositions include humectants, abrasives, surfactants, sweeteners and flavors. The compositions employed in the form of paste and/or powder contain additional ingredients for special functional or aesthetic reasons, for example, fluoridating or coloring agents. The additional ingredients may increase the cost of the product and lead to several side affects.

Another drawback of pastes and gels is to ensure that the products have right consistency, stability, and compatibility of the ingredients employed in the formulation.

Toothpastes and gels are widely accepted dental care agents than tooth powders, since they are more convenient to use. These dental care agents may be delivered as other formulations such as tablets and capsules which will have certain advantages over the most preferred toothpastes and tooth powders.

Humectants, thickeners, coloring agents and water serve no useful purpose in the actual cleaning of teeth, but are employed to impart desirable properties to form paste or gel. These ingredients can be avoided in the delivery system of dental care tablets or capsules.

Capsules of tooth cleansing composition available in the market consist of the same composition as that of toothpaste and gel. However, the mode of delivery of these toothpaste and gel is in capsule form. Such forms of delivery system would not help in reducing cost or avoiding side affects of many synthetic ingredients.

It is therefore necessary to develop a dental care agent that is devoid of unnecessary ingredients to provide a composition containing different herbal extracts of selected herbs and naturally derived excipients.

RELATED ART

U.S. Patent application No. 20070154409 by Annis David et al. teaches the method of converting the composition of toothpowder in to a tablet form. Wherein, the tablet dimensioned and configured to be easily inserted into the mouth and broken up into a paste by chewing for teeth cleaning.

U.S. Pat. No. 7,074,390 by Mackinnon et al. reveals about the preparation of single use dentifrice in a capsule form. The dentifrice may include miswak fibers along with choline and albumin for coating purpose.

SUMMARY OF THE INVENTION

It is a principal object of the present invention to provide a herbal dental care composition comprising extracts of selective natural aromatic and medicinal herbs and the naturally derived excipients, which obviates the drawbacks associated with the dental care composition known in the art.

Further object is to provide high-quality herbal dental care composition having ability to provide the effective protection to the user's teeth and free them from any toxicity, toxic residues and irritation when used.

The above and the other objects of the present invention are attend according to following preferred embodiments of the present invention, however the scope of the invention is not restricted to the particular embodiment.

In accordance with one preferred embodiment of the present invention, there is provided a herbal dental care composition, wherein said composition comprising a herbal extract blend containing effective amount of the extracts of *Punica granatum, Acacia arabica, Terminalia chebula, Terminalia bellerica, Emblica officinalis,* and *Embelia ribes* and pharmaceutically acceptable naturally derived excipients.

In accordance with one preferred embodiment of the present invention, there is provided a herbal dental care composition, wherein said herbal extract blend containing effective amount of the extracts of *Punica granatum, Acacia arabica, Terminalia chebula, Terminalia bellerica, Emblica officinalis,* and *Embelia ribes* is optionally mixed with extract of *Azadirachta indica*.

In accordance with another preferred embodiment of the present invention, there is provided a herbal dental care composition, wherein said composition comprising therapeutically effective amount of extract of *Azadirachta indica* and herbal extract blend containing extracts of *Punica granatum, Acacia arabica, Terminalia chebula, Terminalia bellerica, Emblica officinalis,* and *Embelia ribes* and pharmaceutically acceptable naturally derived excipients.

In accordance with another embodiment of the present invention, there is provided a process for extraction of said extracts of herbs, wherein said extraction process is performed using any suitable extraction technique, preferably a hot-soxhlation or percolation technique and wherein a selective solvent or solvent system are used to yield high extractive value and rich content of stable bioactive ingredients. Said solvent is selected from a group of organic solvents and water, preferably lower chain alcohol/s and water, most preferably selected from methanol and water alone or in combination thereof.

In accordance with another preferred embodiment of the present invention, wherein said extract of herbs can be prepared using all parts of said herbs, preferably bark of *Azadirachta indica* and *Acacia arabica*, preferably fruit rind of *Punica granatum*, preferably fruits of *Terminalia chebula, Terminalia bellerica, Emblica officinalis* and *Embelia ribes*.

In yet another preferred embodiment, there is provided a process for reparation of herbal dental care composition, wherein, the process comprises of extracting the herbal blend of *Punica granatum, Acacia arabica, Terminalia chebula, Terminalia bellerica, Emblica officinalis* and *Embelia ribes* employing suitable solvent, filtering the plant extract, concentrating the plant extract to dryness on a rotatory evaporator or on a steam bath at optimum temperature and producing a herbal composition comprising the resultant dry blend extract and pharmaceutically acceptable naturally derived excipients.

In yet another preferred embodiment, there is provided a process for preparation of herbal dental care composition, wherein, the process comprises of extracting the herbal blend of *Punica granatum, Acacia arabica, Terminalia chebula, Terminalia bellerica, Emblica officinalis* and *Embelia ribes* employing suitable solvent, filtering the plant extract, concentrating the plant extract to dryness on a rotatory evaporator or on a steam bath at optimum temperature and producing a herbal composition by mixing the resultant blend extract with the extract of the herb *Azadirachta indica* and pharmaceutically acceptable naturally derived excipients.

In accordance with another embodiment of the present invention, there is provided a herbal dental care composition, wherein said composition is formulated in various oral delivery system including tablets, capsules, gel, paste, impregnated dental floss etc., preferably tablets, paste or gels, most preferably tablet formulation.

BRIEF DESCRIPTION OF THE DRAWINGS

FIG. 1 is a graph showing the radical scavenging activity of various extracts as disclosed herein.

DETAILED DESCRIPTION OF THE INVENTION

While this specification concludes with claims particularly pointing out and distinctly claiming that, which is regarded as the invention, it is anticipated that the invention can be more readily understood through reading the following detailed description of the invention and study of the included examples.

The present invention provides an herbal dental care composition comprising extracts of *Azadirachta indica, Punica granatum, Acacia arabica, Terminalia chebula, Terminalia bellerica, Emblica officinalis* and *Embelia ribes* and excipients of natural origin. Further, the process to prepare the composition is also disclosed according to present invention.

The disclosed herbal dental care composition, according to the present invention is prepared using effective combination of extract of said herbs *Azadirachta indica, Punica granatum, Acacia arabica, Terminalia chebula, Terminalia bellerica, Emblica officinalis*, and *Embelia ribes* along with the pharmaceutically acceptable naturally derived excipients. The composition is preferably prepared by using herbal extract blend containing extracts of *Punica granatum, Acacia arabica, Terminalia chebula, Terminalia bellerica, Emblica officinalis*, and *Embelia ribes* and the pharmaceutically acceptable naturally derived excipients.

In accordance with further embodiment, said composition can be prepared by mixing herbal extract blend containing extracts of *Punica granatum, Acacia arabica, Terminalia chebula, Terminalia bellerica, Emblica officinalis*, and *Embelia ribes* optionally with herbal extract of *Azadirachta indica* and pharmaceutically acceptable naturally derived excipients, wherein the extract of *Azadirachta indica* used in the composition is preferably in an amount of 0.1% and wherein said herbal extract blend of said herbs in an amount of 0.1% to 5% preferably 1% of herbal blend extract.

The herbal dental care composition according to the present invention possess antibacterial, antiviral, antiseptic, antioxidant and wound healing properties to address the dental disorders such as plaque, dental carries and pyorrhoea.

The used pharmaceutically acceptable naturally derived excipients in the composition, preferably selected from binder, diluent, sweetener, gelling agent, abrasive, foaming agent, flavoring agent and preservative as a carrier or otherwise, wherein, the term "naturally derived excipients" means that excipients used herein are solely selected from the naturally occurring or naturally regenerable resources.

The binder used herein in the composition, according to the present invention, is selected from the group consisting of cellulose per se, esters of cellulose, polymers, gelatins and/or traditional binders alone or in combination thereof, preferably selected from sodium carboxymethylcellulose, hydroxypropyl cellulose, hydroxy propyl methylcellulose, methyl cellulose, polyvinyl pyrrolidone, polyethylene glycol, hydrolyzed gelatin, natural gums, most preferably, selected from hydroxy propyl methyl cellulose (HPMC), corn starch alone or in combination thereof.

The sweetener according to the present invention is selected from natural, artificial, water soluble, water insoluble or intense sweeteners, preferably selected from sucrose, glucose, fructose, fructose syrup, glycyrrhizin, molasses, caramel, mono ammonium salt of glycyrrhizin, mono-, di- or ti-sodium salt of glycyrrhizin, mono-, di- or tri-potassium salt of glycyrrhizin, and calcium salt of glycyrrhizin, sugar alcohols, such as mannitol, sorbitol, xylitol, maltitol alone or in combination thereof. Most preferably, selected from xylitol and glycyrrhizin alone or in combination thereof.

The abrasive according to the present invention is selected from the group comprising natural and synthetic abrasive particulate materials alone or in combination thereof, most preferably, selected from calcium carbonate of natural origin.

The gelling agent according to the present invention is selected from the group comprising natural or synthetic origin alone or in combination thereof, most preferably, selected from xanthum gum of natural origin.

The diluent according to the present invention is selected from the group comprising spray-dried mannitol (Pearlitol.™ SD200), methyl carboxy cellulose alone or in combination thereof.

The foaming agent according to the present invention is selected from the group comprising salts of lauroyl sarcosinate, preferably sodium salt of lauroyl sarcosinate.

The preservative according to the present invention is selected from the group comprising citric acid, sodium benzoate, cetylpyridinium chloride, potassium sorbate and alkyl parabens alone or in combination thereof, preferably potassium sorbate.

The flavoring agent according to the present invention is selected from the group comprising essential oils, flavoring chemicals alone or in combination thereof. Wherein, the essential oils includes oils of spearmint, peppermint, wintergreen, sassafras, clove, sage, eucalyptus, marjoram, cinnamon, lemon, lime, grapefruit and orange and flavoring chemical includes menthol, carvone and anethole. The most preferable flavoring is selected from spearmint oil and menthol alone or in combination thereof.

In accordance with still another embodiment of the present invention is provided with selection and identification of the herbs and obtaining the extracts by subjecting the same to solvent extraction, standardization of these extracts and preparation of the herbal dental care composition using these extracts and other natural origin pharmaceutically acceptable excipients and deliver in the form of chewable tablets for tooth cleansing and treatment for dental disorders.

Example-1

Preparation of the Extract from *Azadirachta Indica* by Percolation Method

The dried material of the bark of *Azadirachta indica* was pulverized to a coarse powder and about 2 kg each of the powdered material was placed in different flasks and extracted with n-hexane, dichloromethane, chloroform, ethyl acetate, acetone, ethanol, methanol and water at room temperature for 24 to 48 h. The plant extracts were then filtered and concentrated to dryness on a rotatory evaporator or on a steam bath at optimum temperature and under reduced pressure. The methanol and water extracts were found to be in good yield.

Example-2

Preparation of the Extract from *Azadirachta Indica* by Hot-Soxhlation Method

The coarse, powdered material of the bark of *Azadirachta indica* was subjected to hot-soxhlation using solvents n-hexane, dichloromethane, chloroform, ethyl acetate, acetone, ethanol, methanol and water at optimum temperature and recycled until the extraction was complete. The plant extracts were then filtered and concentrated to dryness on a rotatory evaporator or on a steam bath at optimum temperature. All the extracts were qualitatively similar to the extracts prepared by the percolation method.

Example-3

Preparation of the Extract from *Punica Granatum* by Percolation Method

The dried material of the fruit rind of *Punica granatum* was pulverized to a coarse powder and about 2 kg of the powdered material was placed in different flasks and extracted with n-hexane, dichloromethane, chloroform, ethyl acetate, acetone, ethanol, methanol and water at room temperature for 24 to 48 h. The plant extracts were then filtered and concentrated to dryness on a rotatory evaporator or on a steam bath at optimum temperature and under reduced pressure. The methanol and water extracts were found to be in good yield.

Example-4

Preparation of the Extract from *Punica Granatum* by Hot-Soxhlation Method

The coarse, powdered material of the fruit rinds of *Punica granatum* was subjected to hot-soxhlation using solvents n-hexane, dichloromethane, chloroform, ethyl acetate, acetone, ethanol, methanol and water at optimum temperature and recycled until the extraction was complete. The plant extracts were then filtered and concentrated to dryness on a rotatory evaporator or on a steam bath at optimum temperature. All the extracts were qualitatively similar to the extracts prepared by the percolation method.

Example-5

Preparation of the Extract from *Acacia Arabica* by Percolation Method

The dried material of the bark of *Acacia arabica* was pulverized to a coarse powder and about 2 kg of the powdered material was placed in different flasks and extracted with n-hexane, dichloromethane, chloroform, ethyl acetate, acetone, ethanol, methanol and water at room temperature for 24 to 48 h. The plant extracts were then filtered and concentrated to dryness on a rotatory evaporator or on a steam bath at optimum temperature and under reduced pressure. The methanol and water extracts were found to be in good yield.

Example-6

Preparation of the Extract from *Acacia Arabica* by Hot-Soxhlation Method

The coarse, powdered material of the bark of *Acacia arabica* was subjected to hot-soxhlation using solvents n-hexane, dichloromethane, chloroform, ethyl acetate, acetone, ethanol, methanol and water at optimum temperature and recycled until the extraction was complete. The plant extracts were then filtered and concentrated to dryness on a rotatory evaporator or on a steam bath at optimum temperature. All the extracts were qualitatively similar to the extracts prepared by the percolation method.

Example-7

Preparation of the Extract from *Terminalia Chebula* by Percolation Method

The dried material of the fruits of *Terminalia chebula* was pulverized to a coarse powder and about 2 kg of the powdered material was placed in different flasks and extracted with n-hexane, dichloromethane, chloroform, ethyl acetate, acetone, ethanol, methanol and water at room temperature for 24 to 48 h. The plant extracts were then filtered and concentrated to dryness on a rotatory evaporator or on a steam bath at optimum temperature and under reduced pressure. The methanol and water extracts were found to be in good yield.

Example-8

Preparation of the Extract from *Terminalia Chebula* by Hot-Soxhlation Method

The coarse, powdered material of the fruits of *Terminalia chebula* was subjected to hot-soxhlation using solvents n-hexane, dichloromethane, chloroform, ethyl acetate, acetone, ethanol, methanol and water at optimum temperature and recycled until the extraction was complete. The plant extracts were then filtered and concentrated to dryness on a rotatory evaporator or on a steam bath at optimum temperature. All the extracts were qualitatively similar to the extracts prepared by the percolation method.

Example-9

Preparation of the Extract from *Terminalia Bellerica* by Percolation Method

The dried material of the fruits of *Terminalia bellerica* was pulverized to a coarse powder and about 2 kg of the powdered material was placed in different flasks and extracted with n-hexane, dichloromethane, chloroform, ethyl acetate, acetone, ethanol, methanol and water at room temperature for 24 to 48 h. The plant extracts were then filtered and concentrated to dryness on a rotatory evaporator or on a steam bath at optimum temperature and under reduced pressure. The methanol and water extracts were found to be in good yield.

Example-10

Preparation of the Extract from *Terminalia Bellerica* by Hot-Soxhlation Method

The coarse, powdered material of the fruits of *Terminalia bellerica* was subjected to hot-soxhlation using solvents n-hexane, dichloromethane, chloroform, ethyl acetate, acetone, ethanol, methanol and water at optimum temperature and recycled until the extraction was complete. The plant extracts were then filtered and concentrated to dryness on a rotatory evaporator or on a steam bath at optimum temperature. All the extracts were qualitatively similar to the extracts prepared by the percolation method.

Example-11

Preparation of the Extract from *Emblica Officinalis* by Percolation Method

The dried material of the fruits of *Emblica officinalis* was pulverized to a coarse powder and about 2 kg of the powdered material was placed in different flasks and extracted with n-hexane, dichloromethane, chloroform, ethyl acetate, acetone, ethanol, methanol and water at room temperature for 24 to 48 h. The plant extracts were then filtered and concentrated to dryness on a rotatory evaporator or on a steam bath at optimum temperature and under reduced pressure. The methanol and water extracts were found to be in good yield.

Example-12

Preparation of the Extract from *Emblica Officinalis* by Hot-Soxhlation Method

The coarse, powdered material of the fruits of *Emblica officinalis* was subjected to hot-soxhlation using solvents n-hexane, dichloromethane, chloroform, ethyl acetate, acetone, ethanol, methanol and water at optimum temperature and recycled until the extraction was complete. The plant extracts were then filtered and concentrated to dryness on a rotatory evaporator or on a steam bath at optimum temperature. All the extracts were qualitatively similar to the extracts prepared by the percolation method.

Example-13

Preparation of the Extract from *Embelia Ribes* by Percolation Method

The dried material of the fruits of *Embelia ribes* was pulverized to a coarse powder and about 2 kg of the powdered material was placed in different flasks and extracted with n-hexane, dichloromethane, chloroform, ethyl acetate, acetone, ethanol, methanol and water at room temperature for 24 to 48 h. The plant extracts were then filtered and concentrated to dryness on a rotatory evaporator or on a steam bath at optimum temperature and under reduced pressure. The methanol and water extracts were found to be in good yield.

Example-14

Preparation of the Extract from *Embelia Ribes* by Hot-Soxhlation Method

The coarse, powdered material of the fruits of *Embelia ribes* was subjected to hot-soxhlation using solvents n-hexane, dichloromethane, chloroform, ethyl acetate, acetone, ethanol, methanol and water at optimum temperature and recycled until the extraction was complete. The plant extracts were then filtered and concentrated to dryness on a rotatory evaporator or on a steam bath at optimum temperature. All the extracts were qualitatively similar to the extracts prepared by the percolation method.

Example-15

Preparation of the Extract from the Herbal Blend by Percolation Method

About 2 kg of the dried, coarse, powdered herbal blend containing the fruit rinds of *Punica granatum* (25%), bark of *Acadia arabica* (20%), fruits of *Terminalia chebula* (10%), fruits of *Terminalia bellerica* (10%), fruits of *Emblica officinalis* (10%) and fruits of *Embelia ribes* (25%) in proportions mentioned in brackets was placed in different flasks and extracted with n-hexane, dichloromethane, chloroform, ethyl acetate, acetone, ethanol, methanol and water at room temperature for 24 to 48 h. The plant extracts were then filtered and concentrated to dryness on a rotatory evaporator or on a steam bath at optimum temperature and under reduced pressure.

Example-16

Preparation of the Extract from the Herbal Blend by Hot Soxhlation Method

About 2 kg of the dried, coarse, powdered herbal blend containing the fruit rinds of *Punica granatum* (25%), bark of *Acadia arabica* (20%), fruits of *Terminalia chebula* (10%), fruits of *Terminalia bellerica* (10%), fruits of *Emblica officinalis* (10%) and fruits of *Embelia ribes* (25%) in proportions mentioned in brackets was subjected hot sox halation extraction with n-hexane, dichloromethane, chloroform, ethyl acetate, acetone, ethanol, methanol and water at room temperature for 24 to 48 h. The plant extracts were then filtered and concentrated to dryness on a rotatory evaporator or on a steam bath at optimum temperature and under reduced pressure. All the extracts were qualitatively similar to those prepared by percolation method.

Example-17

The dried extracts and other pharmaceutically acceptable excipients are combined in a unique combination as described in formula I to V to make a chewable dental care tablets.

Example-18

The following composition comprises formula I (500 mg tablet)

| Extracts | (quantity in mg/tablet) |
|---|---|
| *Azadirachta indica* | 0.72 |
| *Punica granatum* | 1.00 |
| *Acacia arabica* | 0.50 |
| *Terminalia chebula* | 1.00 |
| *Terminalia bellerica* | 1.00 |
| *Emblica officinalis* | 1.00 |
| *Embelia ribes* | 0.50 |
| Pearlitol SD 200 | 239.78 |
| Xylitol | 95.00 |
| HPMC | 15.00 |
| DC Calcium carbonate | 100.00 |
| Potassium sorbate | 2.50 |
| Sodium lauroyl Sarcosinate | 12.00 |
| Xanthum gum | 15.00 |
| Spearmint | 10.50 |
| Menthol | 4.50 |

Example-19

The following composition comprises formula II (500 mg tablet)

| Extracts | (quantity in mg/tablet) |
| --- | --- |
| *Azadirachta indica* extract | 0.72 |
| 2177 B Herbal blend extract | 5.00 |
| Pearlitol SD 200 | 239.78 |
| Xylitol | 95.00 |
| HPMC | 15.00 |
| DC Calcium carbonate | 100.00 |
| Potassium sorbate | 2.50 |
| Sodium lauroyl Sarcosinate | 12.00 |
| Xanthum gum | 15.00 |
| Spearmint | 10.50 |
| Menthol | 4.50 |

Example-20

The following composition comprises formula III (500 mg tablet)

| Extracts | (quantity in mg/tablet) |
| --- | --- |
| *Azadirachta indica* extract | 0.72 |
| 2177B Herbal extract blend | 5.00 |
| Pearlitol SD 200 | 200.28 |
| Xylitol | 95.00 |
| Glycyrrhizin | 4.50 |
| Corn starch | 50.00 |
| DC Calcium carbonate | 100.00 |
| Potassium sorbate | 2.50 |
| Sodium lauroyl Sarcosinate | 12.00 |
| Xanthum gum | 10.50 |
| Spearmint | 10.50 |
| Menthol | 4.50 |

Example-21

The following composition comprises formula IV (500 mg tablet)

| Extracts | (quantity in mg/tablet) |
| --- | --- |
| *Azadirachta indica* extract | 0.72 |
| 2177B Herbal blend extract | 5.00 |
| Pearlitol SD 200 | 129.78 |
| Xylitol | 95.00 |
| DC MCC | 115.00 |
| DC Calcium carbonate | 100.00 |
| Potassium sorbate | 2.50 |
| Sodium lauroyl Sarcosinate | 12.00 |
| Xanthum gum | 15.00 |
| Corn starch | 10.00 |
| Spearmint | 10.50 |
| Menthol | 4.50 |

Example-22

The following composition comprises formula V (500 mg tablet)

| Extracts | (quantity in mg/tablet) |
| --- | --- |
| *Azadirachta indica* extract | 0.72 |
| 2177B Herbal blend extract | 5.00 |
| Pearlitol SD 200 | 234.78 |
| Xylitol | 95.00 |
| Starch | 20.00 |
| DC Calcium carbonate | 100.00 |
| Potassium sorbate | 2.50 |
| Sodium lauroyl Sarcosinate | 12.00 |
| Xanthum gum | 15.00 |
| Spearmint | 10.50 |
| Menthol | 4.50 |

Example-23

The following composition comprises formula VI (500 mg tablet)

| Extracts | (quantity in mg/tablet) |
| --- | --- |
| 2177 B Herbal blend extract | 5.00 |
| Pearlitol SD 200 | 239.78 |
| Xylitol | 95.00 |
| HPMC | 15.00 |
| DC Calcium carbonate | 100.72 |
| Potassium sorbate | 2.50 |
| Sodium lauroyl Sarcosinate | 12.00 |
| Xanthum gum | 15.00 |
| Spearmint | 10.50 |
| Menthol | 4.50 |

Example-24

Manufacturing Process for formula I, II, V, & VI

Weigh accurately *Azadirachta indica* extract, 2177 B herbal blend extract, Pearlitol SD 200, Xylitol and Potassium sorbate as per quantities mentioned in formula I, II & V and pass through #40 mesh for blending up to 5 minutes, weigh the required amount of HPMC (methocel E 15) to disperse in 40 ml of water and make a paste. Add paste into the above powder mix well and pass through #10 mesh and dry the wet granules at about 80-90° C. (Check the moisture content of the granules should between 2-3%) & pass through #16 Mesh, weigh DC Calcium carbonate, Sodium lauroyl sarcosinate, and xanthan gum as per the formula I, II & V and mix with the above granules. Dissolve the required quantities of menthol in spearmint oil and mix with above powder. Compress the final granules into 500 mg Tablets.

Example-25

Manufacturing Process for Formula III & IV

Direct compression method: Weigh accurately *Azadirachta indica* extract, 2177B herbal blend extract, Pearlitol SD 200, Xylitol, and Potassium sorbate, Glycyrrhizin, Corn starch, calcium carbonate DC, Sodium lauroyl sarcosinate and xanthan gum of the required quantity mentioned in Formula III & IV and pass individually through #40 mesh. Blend ingredients for 5 minutes. Dissolve menthol in spearmint and mix with above powder. Compress the above powder into 500 mg tablets.

Example-26

The dried extracts and other pharmaceutically acceptable excipients are combined in a unique combination as described in formula VII to VIII to make a Tooth paste and Tooth gel.

Example-27

The following composition comprises formula VII (Tooth paste)

| Phase | Name of the Ingredients | % use |
|---|---|---|
| A | Xanthan gum | 0.8 |
|   | Glycerine | 5.0 |
| B | Sorbitol | 45.0 |
| C | Neem extract | 0.1 |
|   | 2177 B Herbal blend extract | 1.0 |
|   | Water | Qs |
|   | Sodium Benzoate | 0.5 |
|   | Sodium Saccharin | 0.2 |
|   | Titanium Dioxide | 0.5 |
| D | PEG 600 | 4.0 |
| E | Hydrated silica | 10.0 |
|   | Abrasive silica | 8.0 |
| F | Sodium lauroyl sarcosinate | 3.0 |
| G | Flavor | 1.0 |
|   | Menthol | 0.2 |

Example-28

The following composition comprises formula VIII (Tooth gel)

| Phase | Name of the Ingredients | % use |
|---|---|---|
| A | Cellulose Gum | 0.5 |
|   | Glycerine | 10.0 |
| B | Sorbitol | 57.50 |
| C | Neem extract | 0.1 |
|   | 2177 B Herbal blend extract | 1.0 |
|   | Water | Qs |
|   | Sodium Benzoate | 0.5 |
|   | Sodium Saccharin | 0.2 |
| D | PEG 400 | 3.0 |
| E | Hydrated silica | 8.0 |
|   | Abrasive silica | 6.0 |
| F | Sodium lauroyl sarcosinate | 3.0 |
| G | Flavor | 1.0 |
|   | Menthol | 0.2 |
| H | Color | q.s |

Example-29

Manufacturing Process for Formula VII (Tooth Paste)

1. Disperse xanthan gum in glycerine
2. Add sorbitol to Phase A and mix well
3. Dissolve extract, sodium benzoate, sodium saccharin in water. Disperse Titanium dioxide in phase C
4. Add Phase C to the gum dispersion. Mix Well
5. Add PEG 600 and Mix well
6. Add silica to the above mixture and mix well
7. Apply vacuum to remove entrapped air. Add Sod. Lauroyl sarcosinate under vacuum and mix well
8. Dissolve menthol in flavor and add to the product, mix till uniform

Example-30

Manufacturing Process for Formula VIII (Tooth Gel)

1. Disperse cellulose gum in glycerine
2. Add sorbitol to Phase A and mix well
3. Dissolve extract, sodium benzoate, and sodium saccharin in water.
4. Add Phase C to the gum dispersion. Mix Well
5. Add PEG 400 and Mix well
6. Add silica to the above mixture and mix well
7. Apply vacuum to remove entrapped air. Add Sod. Lauroyl sarcosinate under vacuum and mix well
8. Dissolve menthol in flavor and add to the product, mix till uniform Add color and mix well

Example-31

Antioxidant Activity of Extracts and Herbal Blend Extract by DPPH Method

Radical scavenging activity of individual extracts viz. *Azadirachta indica*, *Punica granatum*, *Acacia arabica*, Triphala (*Terminalia chebula*, *Terminalia bellerica* and *Emblica officinalis*) and *Embelia ribes* and herbal blend extract as per reported DPPH method and results are summarized in FIG. 1.

Example-32

Antibacterial Activity of Herbal Blend Extract and Individual Extracts Against *Streptococcus Mutans*

The *Streptococcus mutans* strain was obtained from IMTECH, Chandigarh, was cultured and maintained on Brain heart Infusion agar media. The minimum inhibitory concentration (MIC) assay for the drugs were determined by using three different methods.

a) E-test: Sterile filter paper discs were coated with different concentrations of the drug and placed over the inoculated lawn of the test organism on the Muller Hinkton agar media and incubated at 37° C. for 24 hrs. Clear zone of bacterial growth inhibition was determined visually, measured and recorded.

b) Micro-plate assay: The experiment was carried using 96 well micro titre-plates where the drugs were diluted as per the required concentration in muller hinkton broth and loaded in to the microtitre well later the test organism was inoculated in to it and incubated at 37° C. for 24 hrs. Growth or inhibition of bacteria was determined by absorbance at 630 nm and results were recorded.

c) Agar Dilution method: The experiment was carried out using sterile 30 mm Plastic petridishes. The required concentration of the drugs were added in to petridishes and mixed with the molten muller hinkton agar media and allowed for solidification. The test organism was spot inoculated over the agar media and incubated at 37° C. for 48 hrs. Results were recorded by visual observation of test organism grown.

Results: The herbal blend extract 2177 B showed MIC values at 5 mg/ml concentration while other extracts *Azadirachta indica*, *Punica granatum* and *Acacia arabica* showed at 10 mg/ml concentration and *Terminalia bellerica*, *Terminalia chebula*, *Emblica officinalis* and *Embelia ribes* did not show any activity against *Streptococcus mutans*. Results are summarized in Table-1

TABLE 1

| S. No | Name of the Extract | MIC value (mg/mL) |
|---|---|---|
| 1 | Herbal blend extract 2177 B | 5 mg |
| 2 | *Punica granatum* | 10 mg |
| 3 | *Azadirachta indica* | 10 mg |
| 4 | *Acacia arabica* | 10 mg |
| 5 | *Terminalia bellerica* | Not detected |
| 6 | *Terminalia chebula* | Not detected |
| 7 | *Emblica officinalis* | Not detected |
| 8 | *Embelia ribes* | Not detected |

Example-33

Clinical Evaluation of Efficacy and Safety of Herbal Toothpaste in Plague Formation A clinical trial of herbal toothpaste was conducted in 60 normal healthy volunteers for 6 weeks. All volunteers were advised to brush the teeth with herbal toothpaste twice daily with soft brush.

Results: A significant reduction ($p < 0.01$) was observed in both plaque index and gingival index in volunteers using Herbal Toothpaste after 6 weeks of usage. There was a significant reduction in microbial growth of *Staphylococcus saprophyticus* and *Staphylococcus ludgenesis* at the end of 6 weeks treatment compared to pretreatment values. There were no adverse drug reactions observed or reported during the entire study period. Results are given in table 2-3.

TABLE 2

Clinical Trial on the Effect of Herbal Toothpaste

| Parameter | Scores on week | | | | | | |
|---|---|---|---|---|---|---|---|
| | 0 | 1 | 2 | 3 | 4 | 5 | 6 |
| Plaque Index | 1.29 ± 0.41 | 1.21 ± 0.36 NS | 1.11 ± 0.34 $p < 0.01$ | 0.95 ± 0.42 $p < 0.01$ | 0.80 ± 0.35 $p < 0.01$ | 0.72 ± 0.35 $p < 0.01$ | 0.68 ± 0.29 $p < 0.01$ |
| Gingival Index | 1.28 ± 0.45 | 1.14 ± 0.38 NS | 0.97 ± 0.34 $p < 0.01$ | 0.94 ± 0.72 $p < 0.01$ | 0.71 ± 0.38 $p < 0.01$ | 0.54 ± 0.30 $p < 0.01$ | 0.55 ± 0.35 $p < 0.01$ |

Statistical analysis was carried out using repeated measures of ANOVA followed by Dunnett's multiple comparison posthoc test.
All the values are expressed as Mean ± SD

TABLE 3

Clinical Trial on the Effect on Herbal Toothpaste on *Staphylococcus saprophyticus* and *Staphylococcus ludgenesis* parameters

| Parameter | No. of patients | | | | Significance |
|---|---|---|---|---|---|
| | Pretreatment | | Post-treatment | | |
| | Present | Absent | Present | Absent | |
| *Staphylococcus saprophyticus* | 48 | 13 | 20 | 41 | $p < 0.0001$ |
| *Staphylococcus ludgenesis* | 14 | 47 | 0 | 61 | $p < 0.0001$ |

Statistical analysis was carried out using Fisher's Exact test.

While this invention has been described in detail with reference to certain preferred embodiments, it should be appreciated that the present invention is not limited to those precise embodiments. Rather, in view of the present disclosure, which describes the current best mode for practicing the invention, many modifications and variations would present themselves to those skilled in the art without departing from the scope and spirit of this invention.

We claim:

1. An herbal dental care composition comprising effective amounts of extracts of *Punica granatum*, *Acacia arabica*, *Terminaha chebula*, *Terminaha bellerica*, *Emblica officinalis* and *Embelia ribes* and one or more pharmaceutically acceptable naturally derived excipients.

2. The herbal dental care composition according to claim 1, wherein said extracts are in the form of a blend.

3. The herbal dental care composition according to claim 2, wherein the blend comprises about 25% of *Punica granatum* extract, about 20% *Acacia arabica* extract, about 10% of *Terminaha chebula* extract, about 10% of *Terminaha bellerica* extract, about 10% of *Emblica officinalis* extract and about 25% of *Embelia ribes* extract.

4. The herbal dental care composition according to claim 1, wherein said extracts are is obtained from all or any specific part(s).

5. The herbal dental care composition according to claim 1, wherein said composition further comprising an extract of *Azadirachta indica*.

6. The herbal dental care composition according to claim 5, wherein said extract is obtained from all or any specific parts of the *Azadiracta indica*.

7. The herbal dental care composition according to claim 5, wherein said extract of *Azadirachta indica* is obtained from the bark thereof.

8. The herbal dental care composition according to claim 5, wherein the *Azadirachta indica* extract in an amount of about 0.1% of the composition.

9. The herbal dental care composition according to claim 1, wherein said one or more pharmaceutically acceptable excipients are selected from the group consisting of abrasive, binder, sweetener, gelling agent, diluent, foaming agent, preservative and flavoring agent, alone or in combination thereof.

10. The herbal dental care composition according to claim 9, wherein said abrasive is calcium carbonate.

11. The herbal dental care composition according to claim 9, wherein said binder is selected from the group consisting of corn starch and hydroxy propyl methyl cellulose (HPMC), alone or in combination thereof.

12. The herbal dental care composition according to claim 9, wherein said sweetener is selected from the group consisting of xylitol and glycyrrhizin, alone or in combination thereof.

13. The herbal dental care composition according to claim 9, wherein said gelling agent is xanthan gum.

14. The herbal dental care composition according to claim 9, wherein said diluent is selected from the group consisting of spray-dried mannitol and methyl carboxy cellulose, alone or in combination thereof.

15. The herbal dental care composition according to claim 9, wherein said foaming agent is sodium lauroyl sarcosinate.

16. The herbal dental care composition according to claim 9, wherein said preservative is potassium sorbate.

17. The herbal dental care composition according to claim 9, wherein said flavoring agent is selected from the group consisting of spearmint oil and menthol alone, or in combination thereof.

18. The herbal dental care composition according to claim 1, wherein said composition is prepared by a method comprising:
   (i) extracting an herbal blend containing *Punica granatum, Acacia arabica, Terminaha chebula, Terminaha bellerica, Emblica officinalis* and *Embelia ribes* employing a solvent or solvent system;
   (ii) filtering the resultant herbal extract employing a suitable filtering aid;
   (iii) concentrating the herbal extract to dryness on rotatory evaporator or on steam bath at optimum temperature and;
   (iv) producing the dental care composition by mixing the dried herbal extract and one or more pharmaceutically acceptable naturally derived excipients.

19. The herbal dental care composition according to claim 18, wherein an extract of *Azadirachta indica* is mixed into the dental care composition of step (iv).

20. The herbal dental care composition according to claim 18, wherein said extracting is performed employing percolation or hot-soxhlation method.

21. The herbal dental care composition according to claim 18, wherein said solvent or solvent system is selected from the group consisting of any organic solvent and water.

22. The herbal dental care composition of claim 18, wherein said solvent or solvent system is selected from the group consisting of methanol, ethanol and water, alone or in combination thereof.

23. The herbal dental care composition according to claim 1, wherein said composition is formulated in a delivery system selected from the group consisting of tablets, capsules, paste, gel and impregnated dental floss.

24. The herbal dental care composition according to claim 1, wherein said extract of *Acacia arabica* is obtained from bark.

25. The herbal dental care composition according to claim 1, wherein said extract of *Punica granatum* is obtained from fruit rind.

26. The herbal dental care composition according to claim 1, wherein said extracts of *Terminaha bellerica, Terminaha chebula, Emblica officinalis* or *Embelia ribes* are obtained from the fruit thereof.

27. An herbal dental care composition comprising a therapeutically effective amount of an extract of *Azadirachta indica* and an herbal blend extract comprising extracts of *Punica granatum, Acacia arabica, Terminalia chebula, Terminalia bellerica, Emblica officinalis* and *Embelia ribes* and one or more pharmaceutically acceptable excipients.

28. The herbal dental care composition according to claim 27, wherein the herbal blend extract is in an amount of about 0.1% to 5%.

29. The herbal dental care composition according to claim 27, wherein the extract of *Azadirachta indica* extract is in an amount of about 0.1% of the composition.

30. The herbal dental care composition according to claim 27, wherein said composition is prepared by a method comprising:
   (i) extracting *Azadirachta indica* employing a suitable solvent or solvent system;
   (ii) extracting an herbal blend containing *Punica granatum, Acacia arabica, Terminalia chebula, Terminalia belleria, Emblica officinalis,* and *Embelia ribes* employing a suitable solvent or system of solvent;
   (iii) filtering the resultant extracts from step (i) and step (ii) by employing a suitable filtering aid;
   (iv) concentrating the filtered extracts to dryness on a rotatory evaporator or on a steam bath at optimum temperature;
   (v) producing a dental care composition by mixing a therapeutically effective amount of the dry extracts from step (iv) and one or more pharmaceutically acceptable excipients.

31. The herbal dental care composition according to claim 30, wherein said extracting extraction is performed employing percolation or hot-soxhlation method.

32. The herbal dental care composition according to claim 30, wherein said solvent or solvent system selected from any organic solvent and water.

33. The herbal dental care composition according to claim 30, wherein the herbal blend extract comprises about 25% of *Punica granatum* extract, about 20% *Acacia arabica* extract, about 10% of *Terminaha chebula* extract, about 10% of *Terminaha bellerica* extract, about 10% of *Emblica officinalis* extract and about 25% of *Embelia ribes* extract.

34. The herbal dental care composition according to claim 30, wherein said solvent or solvent system is selected from the group consisting of methanol, ethanol and water, alone or in combination thereof.

35. The herbal dental care composition according to claim 27, wherein said composition is formulated in a various delivery system selected from the group consisting of tablets, capsules, paste, gel and impregnated dental floss.

36. The herbal dental care composition according to claim 27, wherein the herbal blend extract is in an amount of about 1%.

* * * * *

UNITED STATES PATENT AND TRADEMARK OFFICE
CERTIFICATE OF CORRECTION

| | |
|---|---|
| PATENT NO. | : 8,114,448 B2 |
| APPLICATION NO. | : 12/139262 |
| DATED | : February 14, 2012 |
| INVENTOR(S) | : Mitra et al. |

It is certified that error appears in the above-identified patent and that said Letters Patent is hereby corrected as shown below:

IN THE DRAWINGS:

At (FIG. 1), line 1, above the Figure, please insert --Figure 1--.

At column 4, line 12, please change "ti-sodium" to --tri-sodium--.

At column 4, line 25, please change "xanthum" to --xanthan--.

At column 8, line 63, please change "Xanthum" to --Xanthan--.

At column 9, line 16, please change "Xanthum" to --Xanthan--.

At column 9, line 37 (Approx.), please change "Xanthum" to --Xanthan--.

At column 9, line 58, please change "Xanthum" to --Xanthan--.

At column 10, line 11, please change "Xanthum" to --Xanthan--.

At column 10, line 30, please change "Xanthum" to --Xanthan--.

At column 10, line 41, please change "formula I," to --Formula I,--.

At column 12, line 44, please change "Muller Hinkton" to --Mueller Hinton--.

At column 12, line 50, please change "muller hinkton" to -- mueller hinton--.

At column 12, line 58, please change "muller hinkton" to --mueller hinton--.

At column 13, line 20, please change "Plague" to --Plaque--.

IN THE CLAIMS:

At column 14, line 8, in Claim 1, please change "*Terminaha*" to --*Terminalia*--.

Signed and Sealed this
Third Day of July, 2012

David J. Kappos
*Director of the United States Patent and Trademark Office*

CERTIFICATE OF CORRECTION (continued)
U.S. Pat. No. 8,114,448 B2

At column 14, line 8, in Claim 1, please change "*Terminaha*" to --*Terminalia*--.

At column 14, line 16, in Claim 3, please change "*Terminaha*" to --*Terminalia*--.

At column 14, line 16, in Claim 3, please change "*Terminaha*" to --*Terminalia*--.

At column 14, line 20, in Claim 4, please change "are is" to --are--.

At column 14, line 21, in Claim 4, please change "part(s)." to --part(s) thereof.--.

At column 14, line 27, in Claim 6, please change "*Azadiracta*" to --*Azadirachta*--.

At column 15, line 18 (Approx.), in Claim 18, please change "*Terminaha*" to --*Terminalia*--.

At column 15, line 18 (Approx.), in Claim 18, please change "*Terminaha*" to --*Terminalia*--.

At column 15, line 52, in Claim 26, please change "*Terminaha*" to --*Terminalia*--.

At column 15, line 53, in Claim 26, please change "*Terminaha*" to --*Terminalia*--.

At column 16, line 32, in Claim 31, after "extracting" please delete "extraction".

At column 16, line 40, in Claim 33, please change "*Terminaha*" to --*Terminalia*--.

At column 16, lines 40-41, in Claim 33, please change "*Terminaha*" to --*Terminalia*--.

At column 16, line 48, In Claim 35, after "in a" please delete "various".